US009649269B2

(12) United States Patent
Bosco et al.

(10) Patent No.: US 9,649,269 B2
(45) Date of Patent: May 16, 2017

(54) USE OF GLYCOSAMINOGLYCAN LIPOATE ESTERS IN THE TRICHOLOGY FIELD (71) Applicant: SIGEA S.R.L., Trieste (IT)

(72) Inventors: Marco Bosco, Trieste (IT); Luca Stucchi, Trieste (IT); Matteo Fabbian, Trieste (IT); Fabrizio Picotti, Trieste (IT)

(73) Assignee: SIGEA S.R.L., Trieste (IT)

( * ) Notice: Subject to any disclaimer, the term of this patent is extended or adjusted under 35 U.S.C. 154(b) by 0 days.

(21) Appl. No.: 15/062,406

(22) Filed: Mar. 7, 2016

(65) Prior Publication Data

US 2016/0256376 A1 Sep. 8, 2016

Related U.S. Application Data (62) Division of application No. 13/993,572, filed as application No. PCT/EP2011/072572 on Dec. 13, 2011, now Pat. No. 9,314,418.

(30) Foreign Application Priority Data

Dec. 15, 2010 (IT) .............................. MI2010A2296

(51) Int. Cl.
| | | |
|---|---|---|
| *A61K 8/73* | (2006.01) | |
| *A61Q 5/00* | (2006.01) | |
| *A61Q 5/02* | (2006.01) | |
| *A61Q 7/00* | (2006.01) | |
| *A61Q 5/12* | (2006.01) | |
| *A61K 8/02* | (2006.01) | |
| *A61K 8/06* | (2006.01) | |
| *A61K 8/27* | (2006.01) | |
| *A61Q 5/06* | (2006.01) | |

(52) U.S. Cl.
CPC ............ *A61K 8/735* (2013.01); *A61K 8/0216* (2013.01); *A61K 8/062* (2013.01); *A61K 8/27* (2013.01); *A61K 8/736* (2013.01); *A61Q 5/006* (2013.01); *A61Q 5/02* (2013.01); *A61Q 5/06* (2013.01); *A61Q 5/12* (2013.01); *A61Q 7/00* (2013.01); *A61K 2800/596* (2013.01)

(58) Field of Classification Search
CPC ...... A61K 8/736; C07C 323/52; C07C 327/22
See application file for complete search history.

(56) References Cited

U.S. PATENT DOCUMENTS

| | | | | |
|---|---|---|---|---|
| 6,932,976 | B2 * | 8/2005 | Brooks | ................... A61K 8/27 424/400 |
| 2003/0180337 | A1 | 9/2003 | Streicher et al. | |
| 2009/0304758 | A1 | 12/2009 | Soranzo et al. | |
| 2010/0255097 | A1 | 10/2010 | Picotti et al. | |

FOREIGN PATENT DOCUMENTS

| | | |
|---|---|---|
| CN | 1593373 A | 3/2005 |
| JP | 2007099703 | 4/2007 |
| WO | 2006117995 A1 | 11/2006 |
| WO | 2007105884 A1 | 9/2007 |
| WO | 2009080220 A1 | 7/2009 |

OTHER PUBLICATIONS

International Search Report and Written Opinion of PCT/EP2011/072572 of Mar. 23, 2012.

* cited by examiner

*Primary Examiner* — Nannette Holloman
(74) *Attorney, Agent, or Firm* — Silvia Salvadori, P.C.; Silvia Salvadori (57) ABSTRACT Disclosed is the use of glycosaminoglycan esters, whose alcohol groups are partly esterified with lipoic acid or with lipoic acid and formic acid, in hair care treatments.

6 Claims, 9 Drawing Sheets

Curl retention test

FIGURE 7

Shine test

FIGURE 8

Moisturising test

FIGURE 9

USE OF GLYCOSAMINOGLYCAN LIPOATE ESTERS IN THE TRICHOLOGY FIELD

This application is a Divisional application of U.S. application Ser. No. 13/993,572 filed on Jul. 12, 2013, which is a U.S. National Stage of PCT/EP2011/072572 filed on Dec. 13, 2011, which claims priority to and the benefit of Italian Application No. MI2010A002296, filed on Dec. 15, 2010, the contents of which are incorporated herein by reference in their entireties.

The present invention discloses the use of lipoic esters and mixed lipoic-formic esters of glycosaminoglycans (GAGs) as functional substances for cosmetic and skin-protection use which have a film-forming and protective action on the keratin of the hair shaft, a protective action against attack by free radicals, and a follicle-revitalising, reinforcing, hair-loss preventing action.

The invention also relates to topical preparations with protective, reinforcing and hair-loss preventing activity containing said glycosaminoglycan esters.

The preparation of said esters, in particular esters of hyaluronic acid (HA) and chondroitin sulfate (CS), is disclosed in WO 2009/080220.

STATE OF THE ART

Hyaluronic acid is a ubiquitous endogenous polysaccharide present in numerous parts of the body, especially in the synovial fluid, the eyeball, and the extracellular matrix of the dermis. Numerous studies of its biological activity have demonstrated its anti-inflammatory, tissue-regeneration and viscosupplementation properties and its ability to maintain a high degree of tissue hydration; it performs its action as a modulator of ion diffusion in the extracellular matrix and a cell motility regulator. A radical scavenger action has also been cited; however, it is only observed against some reactive species, and its efficacy in this respect is limited.

The extended structure of hyaluronic acid, with its numerous possibilities to link other molecules to the alcohol groups by complete or partial substitutions, has proved to be the ideal carrier system for small active molecules. These novel polymer compounds act as systems of controlled release of small active constituents to the body surfaces, while the basic structure of hyaluronic acid guarantees adherence and total biological compatibility during all stages of release. The combination of hyaluronic acid and lipoic acid is an example of this type of active connection.

Lipoic acid is an essential cofactor in various multi-enzyme complexes at mitochondrial level, for the metabolism of carbohydrates and proteins, and is involved in the ATP production mechanism. Actions counteracting free radicals and oxidative stress, chelation of metals and regeneration of other antioxidant molecules such as glutathione and vitamins C and E, have also been experimentally demonstrated.

Due to its special chemical structure, with a disulphide bridge in a five-membered ring, and at the low redox potential of the lipoate/dihydrolipoate system, alpha-lipoic acid participates in the reactions of removal of reactive oxygen species (ROS) such as hydroxyl, superoxide, peroxide, singlet oxygen and the free radical nitric oxide. It also reacts very rapidly with non-radical oxidising species such as hypochlorite or $H_2O_2$ which degrade the protein structures, generating radical forms. Moreover, lipoic acid chelates transition metals (like iron and copper) which catalyse the reactions that generate free radicals, and thus neutralises the degradation agents upstream.

Although it is increasingly employed as a diet supplement, lipoic acid is less commonly used for cosmetic purposes due to its impracticality. It is insoluble in water as such, while the solubility of the sodium salt is limited by the pH, which must be at least 7.4. The current topical applications of lipoic acid are almost solely limited to the dermocosmetic field and relate to anti-aging formulations, skin depigmenting agents and formulations for the treatment of inflammations, hypertrophic and keloid scars, rosacea, acne and the resulting scars.

In cosmetics, the use of HA is mainly claimed as a moisturising agent, and the claims relate to the unmodified native molecule, the main characteristic of which relates to the specific molecular weight used. Applications of HA in the trichology field are more recent than those designed for the face/body. U.S. Pat. No. 5,340,579 claims the use of complex mixtures of glycosaminoglycans for the treatment of pathological states of the skin and hair. These mixtures also include HA with a very high molecular weight (2.5-3.0*$10^6$ dalton) and, in particular, proteoglycans extracted from human umbilical cord. The authors do not clarify the action mechanism or nature of the really active ingredients of the mixture; however, they claim that the peptide chains of "proteohyaluronic acid" present in the umbilical cord extract play an essential role in increasing transdermal absorption of the other ingredients with a highly moisturising action.

JP 2007113921 (EP 2166022) discloses the trichological use of products based on esterified HA on the glucuronic acid carboxyl group with residues which have a quaternary ammonium group.

DE 4419783 discloses a medicated shampoo containing esters of lipoic acid and of dihydrolipoic acid as active agents in inhibiting the enzyme responsible for the catabolism of elastin. Moreover, an anti-inflammatory action is attributed to the R enantiomer of lipoic acid, and an analgesic action to the S enantiomer.

JP 62-175417 reports the activity of lipoic acid and hydrophobic derivatives thereof as activator of regrowth in cases of alopecia, a hair-loss prevention action and an anti-dandruff activity.

JP 2008174453, equivalent to WO 2006/117995, discloses the various metabolic actions of dihydrolipoic acid complexed with metals, including inhibition of the enzyme 5 alpha-reductase which converts testosterone to dihydrotestosterone, with a consequent reduction in cell proliferation. Its therapeutic use against alopecia is claimed.

RU 2357722 attributes to lipoic acid the ability to influence cell multiplication in the follicle, stimulating hair regrowth.

JP 2009/137927 discloses the synthesis and use of lipoic acid esters with alcohols of various chemical natures; however, neither saccharides in general nor GAGs in particular are cited.

EP 1890692, equivalent to WO 2006/128618, discloses formulations containing physical mixtures of lipoic acid with hyaluronic acid or derivatives thereof and claims medical applications for skin regeneration, prevention of photoaging and treatment of chronic ulcers and, if administered systemically, for the treatment of neuropathies and poisoning caused by chemical and biological agents. No evidence of its efficacy in cosmetic or hair care treatments is cited.

WO 2009/080220 describes the synthesis and preparation process of ester and amide derivatives of lipoic acid on polysaccharides.

US 2003/180337 describes the use of the R enantiomer of lipoic acid in cosmetic compositions for the skin or hair.

WO 2007/105854 describes esters including lipoic acid and PEG, and claims their topical application for cosmetic use as an elasticising, whitening, antiradical, anti-itching, anti-dandruff and hair regrowth promoting agent. In other words, lipoic acid is "pegylated" to improve its stability. According to the same authors, PEG-lipoate is absorbed through the skin more rapidly/effectively than lipoic acid alone (1.6 times more); conversely, polysaccharide lipoates guarantee prolonged residence of lipoic acid on the surface of the hair shaft, where a barrier to external oxidising agents is stabilised, and maintains physiological hydration due to the moisturising properties of the GAGs. In particular, HA binds lipoic acid to the areas where the polysaccharide accumulates, namely on the hair shaft and in the hair follicle (Novozyme poster, Society of Cosmetic Chemists, Annual Meeting: New York (USA), Dec. 8-9, 2005). No mention is made of any improvement in the efficacy of pegylated lipoate in limiting hair loss, or of a reinforcing/fortifying action.

The various documents of the prior art clearly emphasise the need to use forms of lipoic acid which are expensive and difficult to obtain (the mixture with an enantiomeric excess for the R isomer in US 2003/180337) or unstable (the reduced dihydrolipoic—DHL form in WO 2006/117995), so that they need to be complexed with metals or polyethylene glycols to guarantee their stability. Only these forms are acknowledged to be effective, implicitly excluding the racemate in the more stable form.

However, it has been found that chemical conjugation of the lipoic acid racemate in the most common and stable form with hyaluronic acid (HA) is very effective in strengthening the hair and reducing hair loss. This efficacy is unexpected in view of the findings of said prior art. Moreover, chemical conjugation with hyaluronic acid solves the problem of industrial availability of dihydrolipoic acid (DHL) and of the mixture with R-enantiomer excess.

The present invention is therefore based on the discovery of the surprising performance in protecting and inhibiting hair loss observed after application of a lotion based on HA lipoate. The chemical structure and preparation process of this ester have already been described in the preceding patent for the product. The performance of this ester derives from its chemico-physical and biological properties, which originate from the chemical conjugation of two molecules with different functionalities.

The outcomes of the chemico-physical characterisations and cosmetic functionality tests in vitro and in vivo on the formulations based on HA ester lipoate make the trichological application according to the invention both novel and innovative.

DESCRIPTION OF THE INVENTION

The present invention claims the use of glycosaminoglycans boosted with an active antioxidant, lipoic acid, which is strongly lipophilic and potentially reactive towards thiol groups present on keratin. The polymers are also highly biocompatible because they consist of constituents already present in the body. Chemical conjugation with the polysaccharide modifies the cutaneous absorption of lipoic acid and its preferential distribution in the fatty tissues, and prolongs its residence in the surface layers of the skin and hair. A very high local concentration of lipoic acid in the polymer accumulation areas is obtained in this way.

Hyaluronic acid is known to be mainly concentrated in the hair follicle (Novozyme poster, Society of Cosmetic Chemists, Annual Meeting: New York (USA), Dec. 8-9, 2005); if used in a topical lotion, the polymer fraction which remains adhering to the hair shaft also guarantees lengthy residence of the functional groups of lipoic acid.

In formulation terms, using a polysaccharide to carry lipoic acid molecules is one of the strategies employed to facilitate its dispersion in water and solve the technological problems involved in the manufacture of the related industrial products.

The formulations according to the invention contain a quantity of polysaccharide derivatives which ranges between 0.05% and 5% w/w, and comprise creams, foams, ointments, gels, hydrophilic liquids, shampoos, aqueous or water-alcohol lotions, and oil/water or water/oil emulsions.

In the glycosaminoglycan esters usable according to the invention, the carboxyl function of the polysaccharide can be in acid form or salified with alkaline metals, in particular sodium, while the sulphate function, where present, is salified with alkaline metals, in particular sodium.

Glycosaminoglycan esters typically have a molecular weight of between $10^3$ and $10^7$ dalton, preferably between $10^4$ and $10^6$ dalton.

The compositions according to the invention can also contain a zinc salt and/or a silver salt in a molar ratio between 0.1 and 10 of metal to the lipoic acid content.

The degree of substitution (D.S.) of the hydroxyl groups of each single monomer of the polysaccharide can range between 0.01 and 1*N for lipoic esters, where N is the number of free alcohol groups present in the repeating unit, while the degree of esterification of formic acid on the hydroxyls of the polymer is between 0 and 0.2 (ie. lower than or equal to 20% moles/moles). The presence of formic acid is due to the use of formamide at the synthesis stage, but is not essential to the performance of the derivative.

By varying the degree of esterification of the individual constituents, the chemico-physical and rheological characteristics of the derivatives vary, and in general, the formulability is always better than lipoic acid as is. The polysaccharide ester lipoate and formate easily disperses in water, forming a viscoelastic solution comparable with that typical of native GAG. Formulation in transparent aqueous or water-alcohol products is therefore possible without the use of organic solvents.

Secondly, precisely because of their combination, lipoic acid and hyaluronic acid can benefit the hair in terms of a simultaneous moisturising and repair effect. The structure of the shaft surface, namely the cuticle, is guaranteed by hydrogen bonds between aminoacid side chains, hydrophobic interactions, disulphide bridges between cysteine residues and electrostatic interactions between CO and NH groups in the polypeptide chain of the keratin. Water imbalance in the hair and keratin protein breakdown go together, and can be caused by aggressive treatments (dyeing, permanent waves, etc.) and environmental stress (pollution, drying the hair with excessively hot air, etc.). The example of an extreme treatment such as bleaching, which is highly destabilising for the water balance and the structural integrity of the hair, is enlightening. The release of oxygen from hydrogen peroxide induces modifications in the chemical and physical characteristics of the bleached hair. The oxygen acts on the disulphide bonds of the keratin, destroying them and converting them to oxidised compounds of sulphur, causing an alteration in the mechanical properties of the fibres (resistance to extension, ultimate tensile strength, elasticity, deformation) and a variation in their surface characteristics (electrical properties and porosity). It can also modify, and even destroy, keratin chains with water-soluble protein fragments, which are removed from the hair with the rinsing water. This degradation very probably continues even after the bleaching operation: each subsequent wash can involve the elimination of oligopeptides. The result is dry hair, which is difficult to untangle, weak (lower ultimate tensile strength), more porous and more predisposed to absorb non-self molecules and water. It thus becomes more sensitive to variations in atmospheric humidity, and takes longer to dry. Finally, due to the increase in the number of anionic sites deriving from oxidation of the disulphide bridges and the facility of internal diffusion, the hair absorbs and retains cationic substances more easily, but often unevenly. A substance like alpha-lipoic acid, which is able to bond the free thiol groups of keratin, counteracts the reduction in the disulphide bridges, maintaining the three-dimensional protein structure and the intactness of the capillary fibre. Due to its excellent hydrocoordinating properties, hyaluronic acid forms a hydrated moisturising film which is permeable to air and light, lubricant, not sticky, and viscoelastic, provides the hair surface, gradually and continuously, with a constant quantity of water, and slowly releases alpha-lipoic acid, with a capillary repair effect.

Due to the chemical conjugation of lipoic acid on the polysaccharide, factors such as the presence of metal ions (Cu, Fe) and ultraviolet radiation, which are normally harmful to the hair due to catalytic action in the generation of radicals, combine to stabilise the protective barrier of the product on the hair, thus improving its efficacy.

It is known that lipoic dihydrolipoic acid conversion can be induced by light; in this way —SH functions are generated which are able to bond to the thiol groups of keratin. As the lipoic acid remains covalently bonded to HA, this mechanism further improves the anchorage and residence of the whole polymer on the hair shaft. The polymer film that coats the hair hydrates it, compacts its surface and protects it against subsequent attack by oxidising species. It acts as "adhesive" in the microcracks and between the scales of the keratin, reducing desquamation of the hair. The scheme for formation of bonds with keratin can be described as follows:

where "A" is the protein component and "R" is the residue of esterified dihydrolipoic acid on HA.

Figure 1:
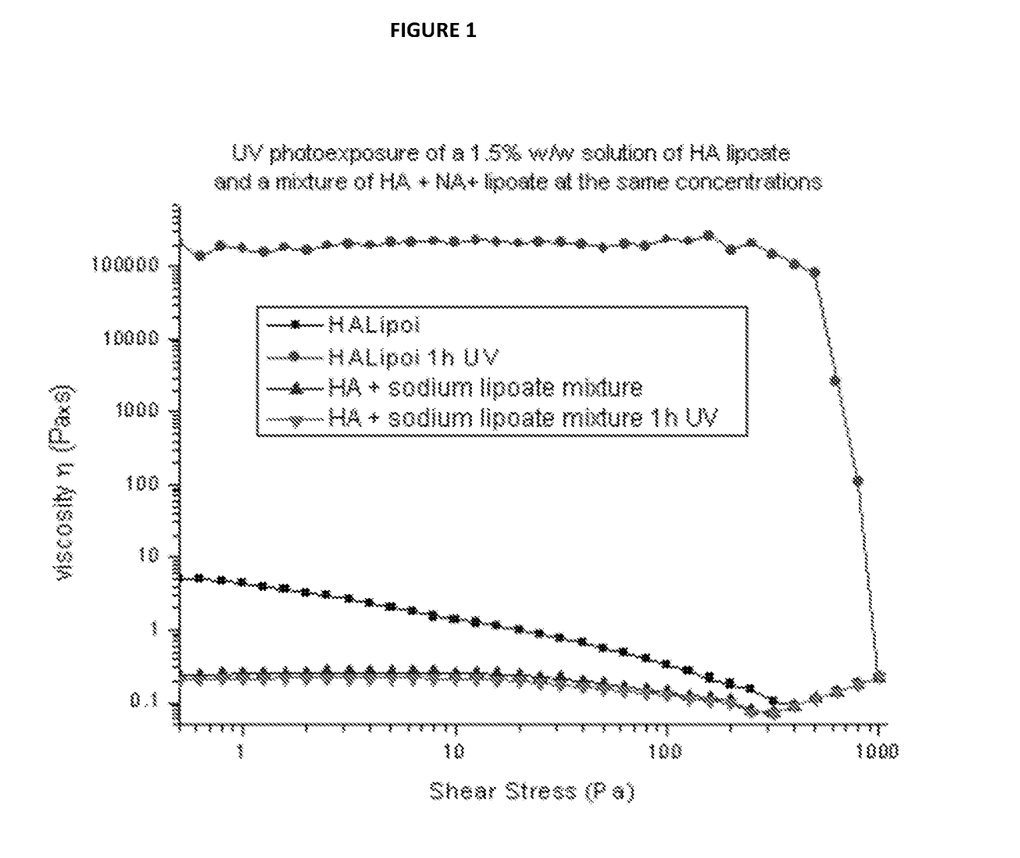
FIG. 1 shows the UV photoexposure of a 1.5% w/w solution of HA lipoate and a mixture of HA, Na and lipoate at the same concentrations.

It has been experimentally demonstrated that said mechanism takes place for the esters according to the invention. An aqueous solution of HA lipoate (D.S.=0.27) at the concentration of 1.5% w/w was placed in a quartz cell for UV spectrophotometry and exposed to UV radiation for one hour (2=254 nm; power=30 watts; distance 20 cm). The cell, closed with a teflon cap, was weighed before and after treatment to rule out the effects of evaporation. After irradiation a cross-linked transparent gel was generated which has a viscosity approx. $10^5$ times greater than the starting solution (see FIG. 1).

For the purpose of comparison, the same treatment was conducted on a physical mixture of HA and lipoic acid contained at the same concentrations as present in the HALip ester: UV irradiation only produces a slight reduction in viscosity attributable to minimal depolymerisation.

The experimental finding of a chemico-physical interaction on the hair shaft, and consequently of anchorage of HALip to keratin, is based on the effect measured in the curl retention test described below.

The interaction with metals also plays an important part in explaining the activity observed.

Metal ions such as Fe, Cu and Zn are present on the skin surface and hair shaft; as already discussed, iron and copper can catalyse the formation of radicals which originate from atmospheric oxygen, and locally give rise to degradation processes.

Figure 2:
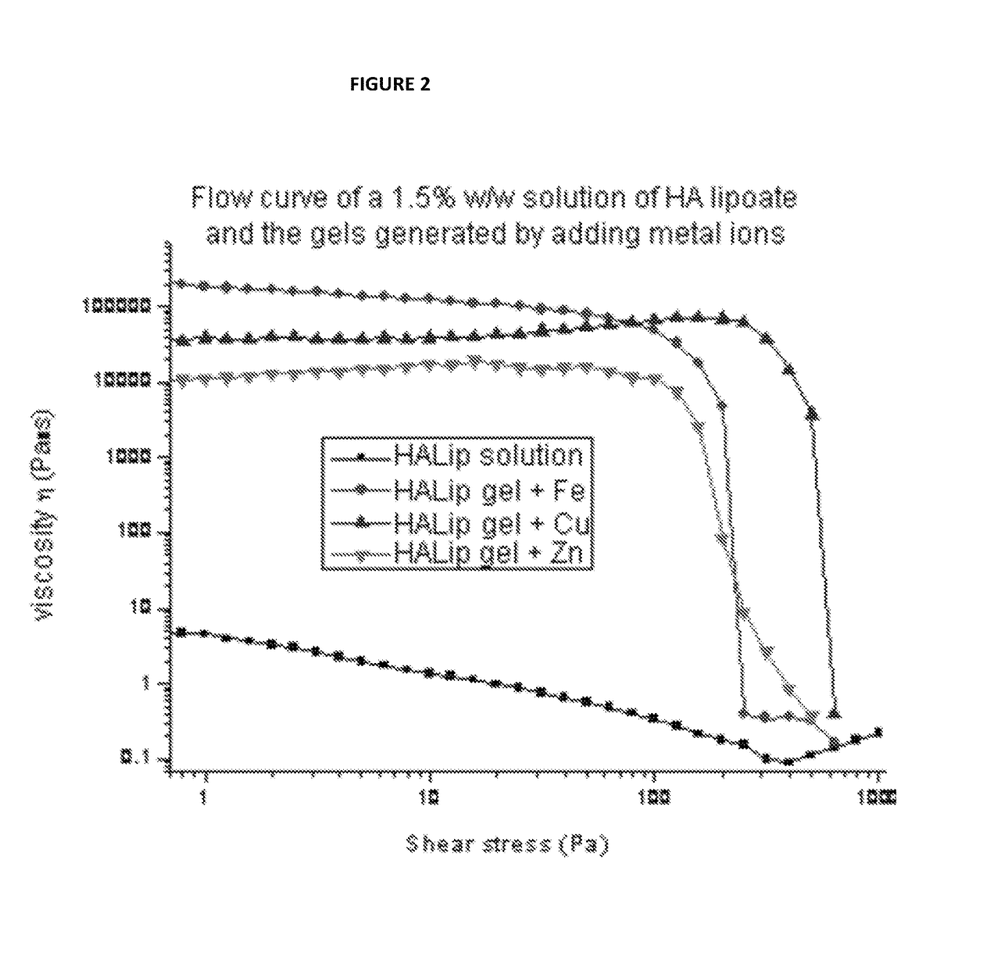
FIG. 2 shows a flow curve of a 1.5% w/w solution of HA lipoate and the gels generated by adding metal ions.

HA lipoate ester is able to sequester these ions, chelating them between two lipoic acid units. FIG. 2 shows the rheological curves of a 1.5% aqueous solution of lipoic HA and of the gels formed from it by adding 1 Fe equivalent, 1 Cu equivalent and 10 Zn equivalents, compared with esterified lipoic acid.

The evidence of crosslinking between the polymer chains induced by the presence of the metal demonstrates the involvement of two units of lipoic acid in complexing the cation. Since in chelation the ester remains stable, a compact three-dimensional mesh of polymer chains is generated which makes the moisturising and protective action even more effective.

For comparison purposes, in the physical mixture of HA and lipoic acid, the interaction only takes place between the latter and the metal, not involving the polysaccharide; the lipoic acid-metal complex becomes insoluble, and produces an amorphous aggregate. The lipoic acid also chelates the metal by means of the carboxyl, forming a different compound from that generated by the ester on HA.

The partial esters of glycosaminoglycans with lipoic acid or with lipoic and formic acid also have a protective activity against aggressive oxidising agents such as hypochlorite and Fenton system.

Hyaluronic acid in itself possesses a radical and oxidising species scavenging action, but this property is considerably enhanced in the conjugate with lipoic acid.

Figure 3:
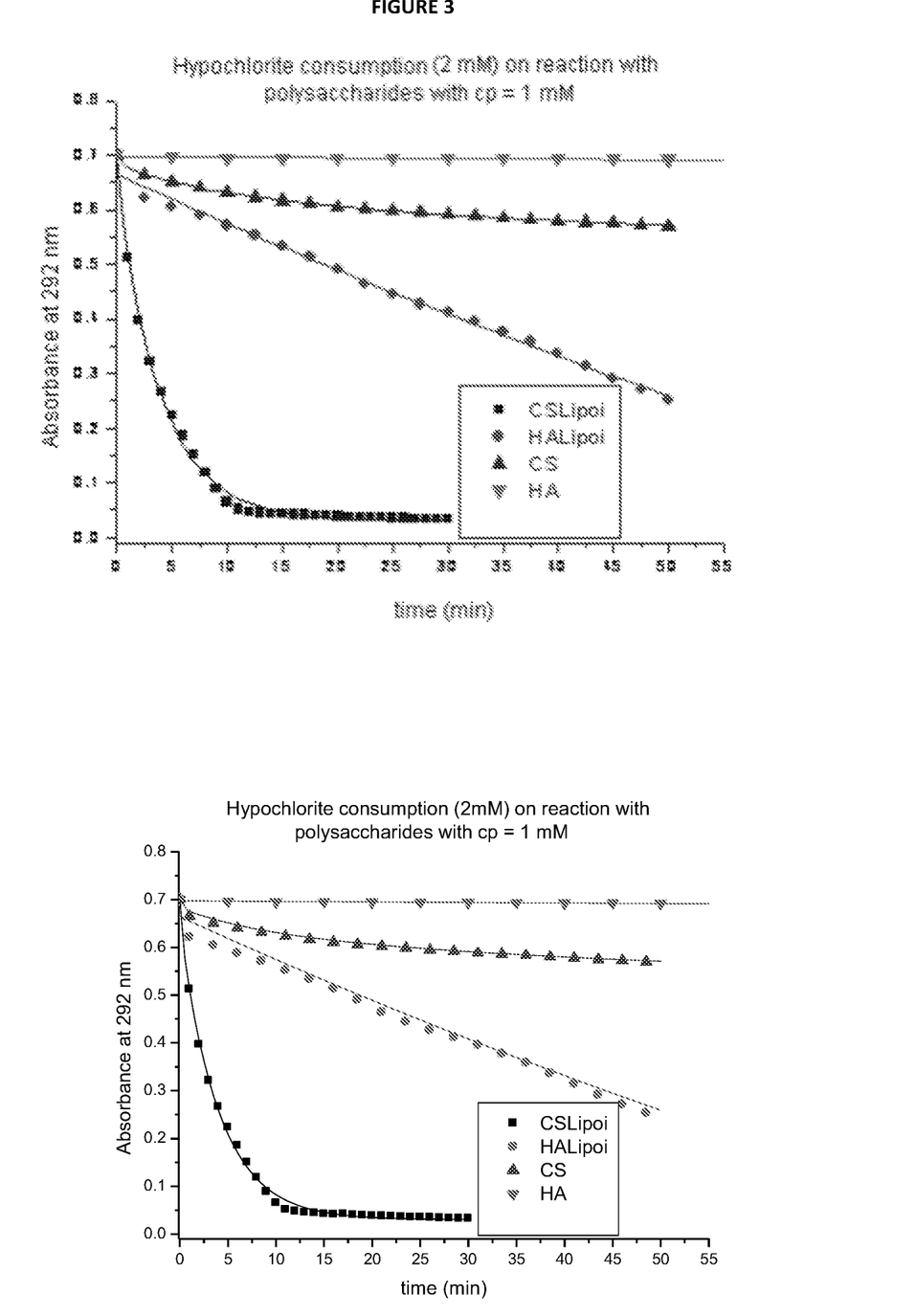
FIG. 3 shows the absorbance of the hypochlorite over time.

The rate of elimination of hypochlorite by HALipoi, CSLipoi, native HA or native CS has been measured in a 2 mM solution. The graphs relating to the kinetics are shown in FIG. 3, which indicates the absorbance of the hypochlorite ion over time: the concentration of the polysaccharides amounts to 1 mM in repeating units; the degree of substitution in lipoic acid (DS) in HALipoi amounts to 0.28; and the DS in CSLipoi amounts to 0.34.

Figure 4:
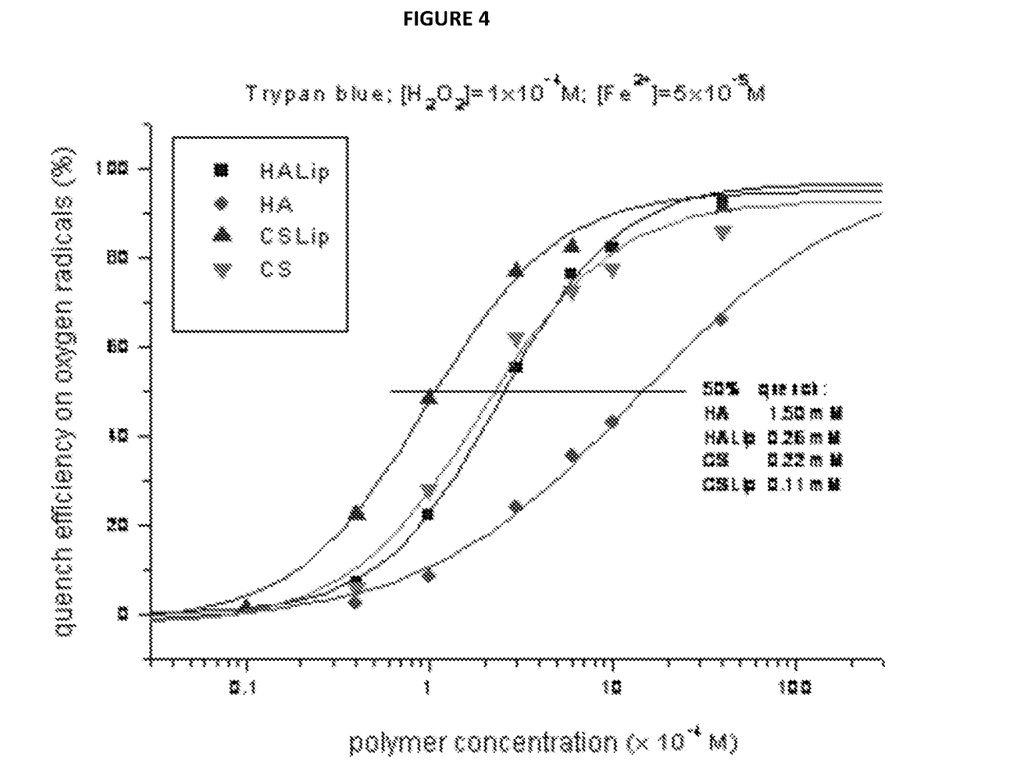
FIG. 4 shows the efficiency of action of the scavenger at various polymer concentrations.

Again in relation to the Fenton system ($H_2O_2$/Fe), which produces oxygen radicals, HA and CS lipoate esters have proved much more effective than the corresponding polysaccharide in eliminating radicals. Solutions containing a dye (Trypan blue) were treated with $H_2O_2$ (0.1 mM) and $Fe^{2+}$ (0.05 mM); the oxygen radicals oxidise the chromophore, whose absorbance at 588 nm falls rapidly over time. Numerous similar solutions also containing HA, CS, HALipoi or CSLipoi, at increasing concentrations (cp), were then prepared. The polysaccharide is able to eliminate the radicals and preserve the dye intact. FIG. 4 shows the efficiency of action of the scavenger at various polymer concentrations.

The cp required to halve the damage caused by radicals to the colouring amounts to 1.5 mM for native HA, and falls to 0.26 mM for HALipoi containing a DS in lipoic acid amounting to 0.28 moles/moles. CS produces this result at the concentration of 0.22 mM. and CSLipoi at cp=0.11 mM.

Protection against enzymatic degradation was also evaluated: the polysaccharide, distributed on the scalp, can easily penetrate the hair follicle cavity, where it comes into contact with viable cells; to perform its action as effectively as possible it is important for it not to be degraded too rapidly by hydrolytic enzymes, especially hyaluronidase. One of the advantages of the invention compared with native hyaluronic acid is that the presence of lipoic or mixed lipoic and formic acid ester substituents protects it against enzymatic degradation. Said innovative property is illustrated by following the enzymatic digestion kinetics through rheological measurements.

Figure 5:
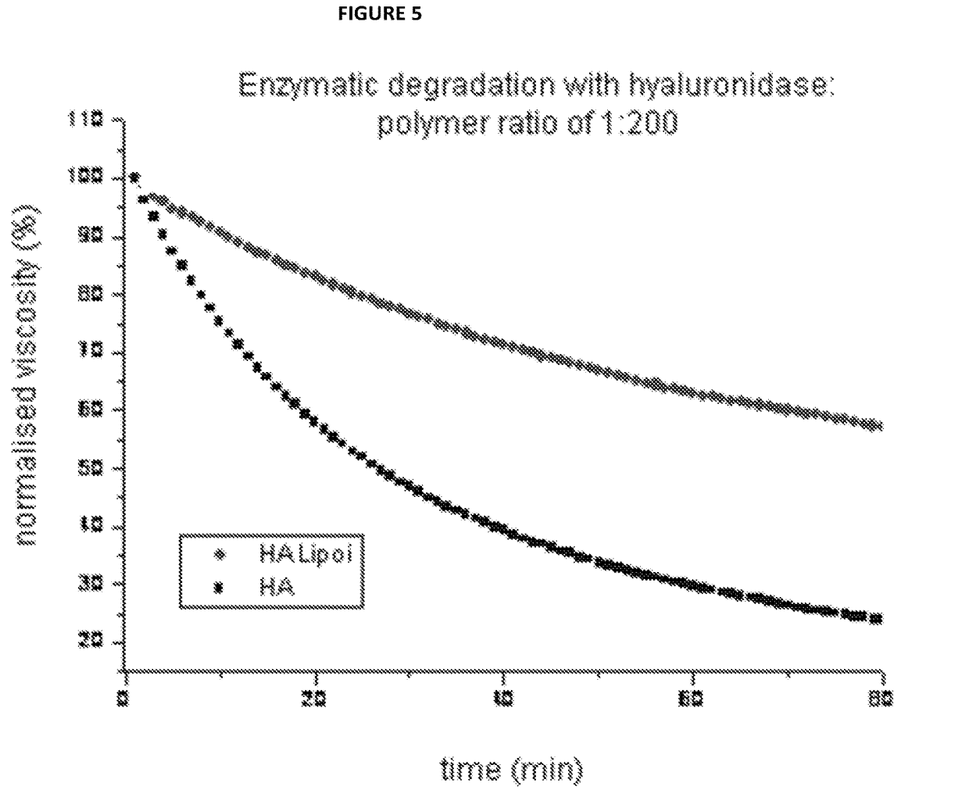
FIG. 5 shows the enzymatic degradation with hyaluronidase: polymer ratio of 1:200.

The study was conducted on a solution of HA and a solution of lipoic HA with D.S.=0.3, described in example 1 below, at the concentration of 1.0% w/w, in acetate buffer. Each hydrolysis kinetics test was carried out by adding approx. 70 μl of a concentrated solution of "endo" bovine testicular hyaluronidase (1060 U/mg) to 1.5 ml of polymer solution to give an enzyme/polymer ratio of 1:200. The mixture is mixed for 30 secs and transferred to the rheometer plate for continuous measurement of the viscosity. The solutions before mixing and the rheometer plates are thermostated at 37° C. FIG. 5 shows the gradual variation in viscosity as the enzyme hydrolyses the polysaccharide. The ester derivative resists the enzymatic action longer than native HA.

On the basis of the factors set out above, it is evident that the compositions according to the invention are useful for hair regenerating, reinforcing and anti-hair loss treatment, and to treat states of androgenic alopecia and telogen effluvium.

The invention is further illustrated by the following examples of preparation of mixed lipoic/formic esters of hyaluronic acid, the corresponding cosmetic formulations and tests of activity in vitro and in vivo.

Example 1

Synthesis of Lipoic and Formic Ester of Hyaluronic Acid Sodium Salt 2 g of HA in 40 ml of FA (5% w/w) is introduced into a 100 ml three-necked flask and the solution is left under mechanical stirring at 90° C., under $N_2$ flow, until complete solubilisation of the polymer. The temperature is then adjusted to room temperature with a water bath.

The lipoic acid (772.1 mg, equal to 0.75 HA equivalents HA) is then solubilised separately in 2 ml of DMSO; solid carbonyldiimidazole (CDI, 667.5 mg, equal to 1.1 lipoic acid equivalents) is then added and left to react at room temperature until complete release of $CO_2$.

At this point 200 mg of $Na_2CO_3$ is introduced into the solution of polymer in FA; the activated lipoic acid is then added, and the solution is left under stirring at room temperature. The solution becomes yellow, transparent and highly viscous (pH~10).

After a reaction time of between 30 minutes and 4 hours, the reaction is blocked by adding 20 mL of $H_2O$ and 14 mL of 0.5 M HCl; the final pH measures 7.05. The final solution, which is slightly viscous, transparent and pale yellow, is purified by dialysis, and the polymer is recovered by freeze-drying.

NMR analysis of the lyophilisate allows the quantification of a degree of substitution in lipoate esters (DSlip) amounting to 0.35 and formate esters (DSform) amounting to 0.07.

Example 2

Synthesis of Chondroitin Sulphate Lipoic and Formic Ester 4 g of chondroitin sulfate (CS) in 20 ml of FA (20% w/w) is introduced into a 100 ml three-necked flask and the solution is left under mechanical stirring at 90° C., under $N_2$ flow, until complete solubilisation of the polymer. The temperature is then adjusted to room temperature with a water bath.

The lipoic acid (984.2 mg, equal to 0.6 HA equivalents) is solubilised separately in 2 ml of DMSO; solid carbonyldiimidazole (CDI, 851.3 mg, equal to 1.1 lipoic acid equivalents) is then added and left to react at room temperature until complete release of gas.

At this point 320 mg of $Na_2CO_3$ is introduced into the solution of polymer in FA; the activated lipoic acid is then added, and the solution is left under stirring at room temperature. The solution becomes yellow and transparent, and remains fluid.

After a reaction time of between 30 minutes and 4 hours, the reaction is blocked by adding 40 mL of $H_2O$ and 14 mL of 0.5 M HCl, which neutralises the pH to 7.15; the final solution, which is slightly viscous, transparent and pale yellow, is purified by dialysis, and the polymer is recovered by freeze-drying.

NMR analysis of the lyophilisate allows the quantification of a degree of substitution in lipoate esters (DSlip) amounting to 0.28 and formate esters (DSform) amounting to 0.05.

Example 3

Preparation of a Reinforcing/Fortifying Water-Alcohol Lotion at the Concentration of 0.2%

| | |
|---|---|
| HA lipoate/formate ester (example 1) | 0.20 |
| Water | 75.04 |
| Denatured alcohol | 20.0 |
| Ethoxydiglycol | 1.2 |
| *Picea abies* extract, pentylene glycol | 1.0 |
| *Swertia japonica* extract, butylene glycol, water | 0.60 |
| Inositol | 0.50 |
| Betaine | 0.50 |
| PPG-26-buteth-26, PEG-40 hydrogenated castor oil, water | 0.30 |
| Tetrasodium glutamate diacetate, water | 0.30 |
| Perfume | 0.15 |
| Caffeine | 0.10 |
| Lactic acid, water | 0.10 |
| Nordihydroguaiaretic acid | 0.01 |

Example 4

Preparation of a Reinforcing/Fortifying Water-Alcohol Lotion at the Concentration of 0.5%

| | |
|---|---|
| HA lipoate/formate ester (example 1) | 0.50 |
| Water | 74.74 |
| Denatured alcohol | 20.0 |
| Ethoxydiglycol | 1.2 |
| *Picea abies* extract, pentylene glycol | 1.0 |
| *Swertia japonica* extract, butylene glycol, water | 0.60 |
| Inositol | 0.50 |
| Betaine | 0.50 |
| PPG-26-buteth-26, PEG-40 hydrogenated castor oil, water | 0.30 |
| Tetrasodium glutamate diacetate, water | 0.30 |
| Perfume | 0.15 |
| Caffeine | 0.10 |
| Lactic acid, water | 0.10 |
| Nordihydroguaiaretic acid | 0.01 |

Example 5

Preparation of a Reinforcing/Fortifying and Soothing Water-Alcohol Lotion Based on 0.2% HA Lipoate and Zinc

| | |
|---|---|
| HA lipoate/formate ester (example 1) | 0.20 |
| Water | 75.02 |
| Denatured alcohol | 20.0 |
| Ethoxydiglycol | 1.2 |
| *Picea abies* extract, pentylene glycol | 1.0 |
| *Swertia japonica* extract, butylene glycol, water | 0.60 |
| Inositol | 0.50 |
| Betaine | 0.50 |
| PPG-26-buteth-26, PEG-40 hydrogenated castor oil, water | 0.30 |
| Tetrasodium glutamate diacetate, water | 0.30 |
| Perfume | 0.15 |
| Caffeine | 0.10 |
| Lactic acid, water | 0.10 |
| Nordihydroguaiaretic acid | 0.01 |
| Zinc Chloride | 0.02 |

Example 6

Preparation of a Reinforcing/Fortifying and Antiseptic Water-Alcohol Lotion Based on 0.2% Chondroitin Sulfate Lipoate and Silver

| | |
|---|---|
| CS lipoate/formate ester (example 2) | 0.20 |
| Water | 75.02 |
| Denatured alcohol | 20.0 |
| Ethoxydiglycol | 1.2 |
| *Picea abies* extract, pentylene glycol | 1.0 |
| *Swertia japonica* extract, butylene glycol, water | 0.60 |
| Inositol | 0.50 |
| Betaine | 0.50 |
| PPG-26-buteth-26, PEG-40 hydrogenated castor oil, water | 0.30 |
| Tetrasodium glutamate diacetate, water | 0.30 |
| Perfume | 0.15 |
| Caffeine | 0.10 |
| Lactic acid, water | 0.10 |
| Nordihydroguaiaretic acid | 0.01 |
| Silver nitrate | 0.02 |

Example 7

Preparation of an O/W Cream

The preparation of a formulation in cream form containing one of the lipoic acid esters according to the invention is described below.

The O/W cream formulation contains, as functional agent, the compound described in example 1 at the concentration of 0.1%, suitably mixed with common excipients used in skin cosmetics, such as emulsifiers, thickeners, oils, moisturisers, gelling agents, preservatives, etc.

Briefly, the process is as follows: Approximately 600 ml of demineralised water (corresponding to approx. 60% by weight of the total formulation) is loaded into a turboemulsifier, and the pre-melted fatty phase is added under stirring at approx. 70° C. The mixture is emulsified, and cooled slowly to the temperature of 35-40° C. The thermolabile and volatile constituents are added at this temperature, followed by the HA sodium salt lipoic ester described in example 1, dissolved in a suitable quantity of water. The mixture is left under slow stirring until the temperature of 25-30° C. is reached, and the finished product is then discharged into a suitable container.

The result is a cream with the following composition (% W/W):

| | |
|---|---|
| Lipoic ester of HA sodium (Example 1) | 0.1 |
| Oils (palmitic/caprylic glycerides-triglycerides) | 12.0 |
| Non-ionic emulsifiers | 6.0 |
| Cetyl alcohol | 2.0 |
| Dimethicone | 4.0 |
| MgAl silicate | 2.0 |
| Glycerin | 3.0 |
| Xylitol | 2.0 |
| Paraben | 0.7 |
| Water q.s. for | 100 |

Example 8

Preparation of a Mousse

The formulation contains, as functional agent, the compound described in example 1 at the concentration of 0.1%, suitably mixed with common excipients used in skin cosmetics, such as emulsifiers, thickeners, oils, moisturisers, gelling agents, preservatives, etc.

The result is a cream with the following composition (% W/W):

| | |
|---|---|
| Lipoic ester of HA sodium (Example 1) | 0.1 |
| Panthenol | 0.3 |
| Niacinamide | 0.15 |
| Cetrimonium chloride | 5.0 |
| Polysorbate 80 | 1.6 |
| Tocopheryl acetate | 0.02 |
| Perfume | 0.2 |
| Hydrolysed silk PG-propyl methylsilanediol | 3.0 |
| Phenoxyethanol, caprylyl glycol | 1.5 |
| 2,4-dichlorobenzyl alcohol | 0.15 |
| Water q.s. for | 100.0 |

Example 9

Preparation of a Mask

The O/W cream formulation contains, as functional agent, the compound described in example 1 at the concentration of 0.05%, suitably mixed with common excipients used in skin cosmetics, such as emulsifiers, thickeners, oils, moisturisers, gelling agents, preservatives, etc.

The result is a cream with the following composition (% W/W):

| | |
|---|---|
| Lipoic ester of HA sodium (Example 1) | 0.05 |
| Panthenol | 0.5 |
| Guar hydroxypropyltrimonium chloride | 0.05 |
| Water, cetrimonium chloride | 6.0 |
| Cetearyl alcohol, cetearyl glucoside | 4.0 |
| Glycol palmitate | 2.0 |
| Isononyl isononanoate | 3.5 |
| Dimethicone | 1.5 |
| Bisabolol | 0.1 |
| Tocopheryl acetate | 0.2 |
| Phenoxyethanol, caprylyl glycol | 1.5 |
| Perfume | 0.5 |
| Cyclopentasiloxane | 1.5 |
| Water, hydrolysed silk PG-propyl methylsilanediol | 1.0 |
| 2,4-dichlorobenzyl alcohol | 0.15 |
| Water q.s. for | 100.0 |

Example 10

Preparation of a Shampoo

A formulation in shampoo form containing, as functional agent, the compound described in example 1 at the concentration of 0.2%, has the following composition (% W/W):

| | |
|---|---|
| Lipoic ester of HA sodium (Example 1) | 0.2 |
| Panthenol | 0.05 |
| Disodium EDTA | 0.15 |
| *Lonicera caprifolium* flower extract, | |
| *Lonicera japonica* flower extract, water | 0.5 |
| Glycerin | 3.0 |
| Sorbitol, water | 0.4 |
| Betaine | 0.5 |
| Xylitylglucoside, anhydroxylitol, xylitol | 1.0 |
| Disodium cocoyl glutamate, water | 10.0 |
| Decyl glucoside, water | 5.0 |
| Sodium cocoyl apple amino acids, water | 3.0 |
| Cocamidopropyl betaine, water | 10.0 |
| Cocamidopropyl PG-dimonium chloride phosphate | 1.0 |
| PEG-120 methyl glucose trioleate, propylene glycol, water | 4.0 |
| PEG/PPG-120/10 trimethylpropane trioleate, laureth-2 | 0.7 |
| Polysorbate 20 | 1.0 |
| Perfume | 0.5 |
| Caprylyl/capryl glucoside | 5.0 |
| Water q.s. for | 100.0 |

Example 11

In Vitro Trichological Tests

The polymer-hair interaction can be demonstrated by measuring some chemico-physical parameters on cut hair shafts treated with lotions based on lipoic HA as described in examples 3 and 4. The most significant tests in this respect are evaluation of shine, curl retention and persistence of hydration on the cut hair.

"Italian Virgin Hair" plaits consisting of straight dark brown hair 16 cm long (LoCurcio—Manifattura Italiana Capelli, Palermo, Italy) were used in the quantitative test. The plaits are divided into test locks weighing approx. 2-3 g, accurately weighed to the second decimal place, and maintained with elasticised cotton. The locks of hair then undergo standard washing with a basic shampoo [Active Washing Substance (SAL)=15%] and dried with an ordinary hairdryer (2000 watts, at maximum speed and airstream heat level), to equalise the surface.

In each test, three locks of hair are treated with the lotion containing 0.2% of active ingredient (P02), three with the 0.5% lotion (P05) and three with the solution of excipients alone, without the functional polymer (P00); finally, three more locks are treated with water alone (STD).

Curl Retention:

The procedure for preparation of the locks of hair involves standard washing, rinsing, treatment with the test lotion, curling and drying with a hairdryer. The locks are then placed under tension and the elongation of the curls is measured after a pre-set time, indicating the combination of plastic deformation and elastic return of the locks of hair.

Figure 6:
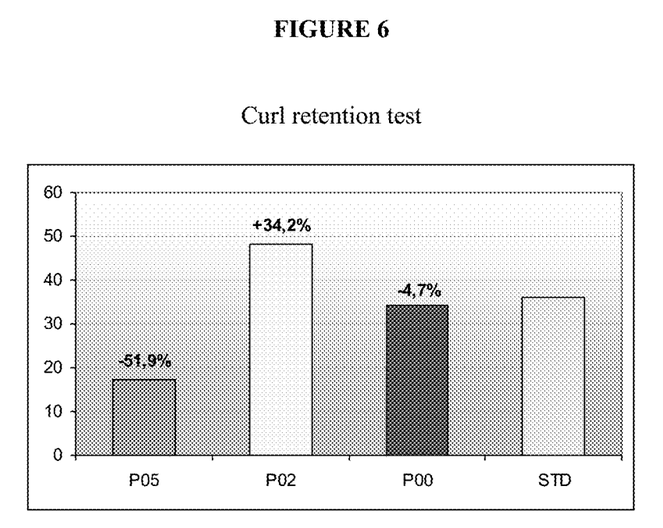
FIG. 6 shows the results of the curl retention test.

FIG. 6 shows the mean elongation in mm and the mean percentage variation in uncurling of the treated locks (P05, P02, P00) in 24 hours, compared with untreated hair (STD). The differences in effects on the samples treated with the lotions and those treated with the placebo were statistically significant.

Hair treatment with lotion P05 improves the elasticity of the hair and helps to maintain the wave of curly or wavy hair, thus proving useful to increase the persistence of the hair shape.

Conversely, a lower polymer content, of around 0.2%, is specified for lotions with a smoothing effect, because they lead to a statistically significant reduction in curl strength compared with locks of hair which undergo the same treatment procedure, but without active ingredients.

Shine:

Shine was measured by the colorimetric method, based on determination of the reflecting power of light on a lock of hair.

The measurement system used for the reading was the $L^*$ $a^*$ $b^*$ system (CIELAB colour space), where:

$L^*$ corresponds to the brightness of the colour. The values of $L^*$ are expressed on a scale of 0 to 100, where 0 corresponds to the colour black and 100 to white.

$a^*$ and $b^*$ indicate the two colour axes, where $a^*$ represents the red axis and $b^*$ the yellow-blue axis.

This study considered the parameter $L^*$ as the index of brightness of the sample, namely its light-reflecting power.

Figure 7:
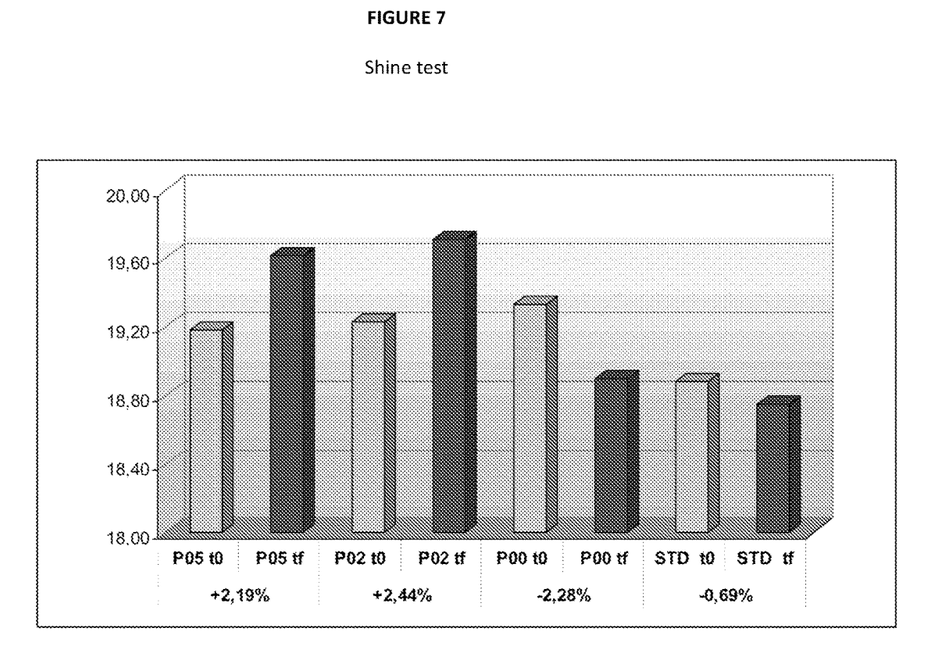
FIG. 7 shows the values of L* measured on the locks of hair before and after treatment.

FIG. 7 shows the values of $L^*$ measured on the locks of hair before and after treatment.

Hair treatment with a lotion containing between 0.2% and 0.5% of HA lipoate increases brightness value $L^*$ after a single application, by approx. +2.2-2.4% compared with the initial values, and approx. +4.7-4.5% compared with the placebo lotion. The differences in effects on the samples treated with the lotions compared with the placebo were statistically significant.

Moisturising

The measurement method was gravimetric, based on the ability of the locks of hair to retain a given level of hydration under pre-set temperature and humidity conditions.

Figure 8:
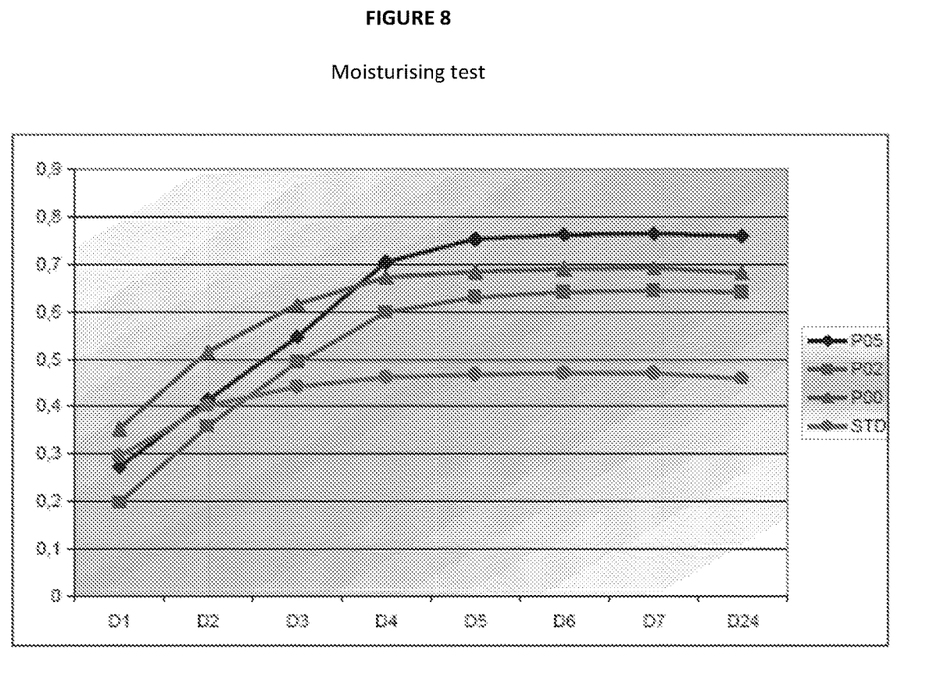
FIG. 8 shows the mean water loss values per gram of hair in 24 hours.

FIG. 8 shows the mean water loss values per gram of hair in 24 hours (D1-D24) for the variously treated groups of locks: P05, P02, P00, STD.

Treatment with lotions containing HA lipoate induces the release of water at a constant rate in the first four hours, regardless of the concentration of active ingredient, with a regular pattern compared with the placebo lotion and the standard. The differences in effects between the samples treated with the lotions and the placebo were statistically significant.

In any event the addition of the polymer helps to maintain the dynamics of water balance of the hair, to the greatest extent in the case of P05.

Example 12

In Vivo Trichological Tests

Evaluation of Sensory Effect

To evaluate the efficacy and tolerability of the hair lotion containing 0.2% HA lipoate, as described in example 3, 40 volunteers used the product once a day for two weeks, applying it in any quantity to the dry hair. At the end of the period of use they expressed their subjective opinions in a questionnaire. The investigator weighed the bottles at the beginning and end of the test to determine the mean amount of product used by the volunteers.

From the responses obtained through the questionnaire, the following findings were made:

85% of volunteers considered the treatment to be fairly or very effective in making the hair less dry;

82.5% of subjects considered the treatment to be fairly or very effective in making the hair soft;

75% of volunteers considered the treatment to be fairly or very effective in making the hair shiny;

67.5% of volunteers considered the treatment to be fairly or very effective in making the hair less fragile;

52.5% of volunteers considered the treatment to be fairly or very effective in preventing and treating split ends;

The volunteers used 28.32 g of the product on average, with a standard deviation of 13.6 g.

In general, the opinions expressed attributed a nutrient action to the lotion, namely the sensation of healthy, robust, stronger hair.

Evaluation of Reinforcing/Fortifying Action 20 subjects (10 women and 10 men) suffering from mild telogen effluvium and androgenic alopecia (Ludwig stage I, Hamilton stage II) were selected for the efficacy evaluation. The volunteers applied 2.5 ml of lotion containing 0.2% HA lipoate, as described in example 3, to the scalp, once a day for 2 months.

Evaluations of tensile strength (pull test) and a count of the hairs lost during washing (wash test) were performed at the beginning and end of the treatment period.

Tensile Strength (Pull Test)

The tensile strength of the hair was evaluated on the basis of the total number of hairs eradicated in three sites (the temporal, frontal and occipital areas) on the following semi-quantitative four-point scale:

0=>6 hairs eradicated in total in the three sites
1=4 to 6 hairs eradicated in total in the three sites
2=1 to 3 hairs eradicated in total in the three sites
3=0 hairs eradicated in total in the three sites.

At the end of the treatment there was a statistically significant increase in the tensile strength of the hair. The mean values of the scores are set out in the following table:

| $T_0$ | $T_{2mesi}$ | variation $T_{2\ months} - T_0$ | Wilcoxon test |
|---|---|---|---|
| mean 1.2 Std. dev. 0.7 | mean 1.7 std. dev. 0.7 | 0.5 (41.7%) | p = 0.01 |

Inhibition of Hair Loss (Wash Test)

At the end of the treatment, the mean variation in the hair count was −50.0% compared with time zero, and proved highly significant on statistical analysis (p<0.001).

Figure 9:
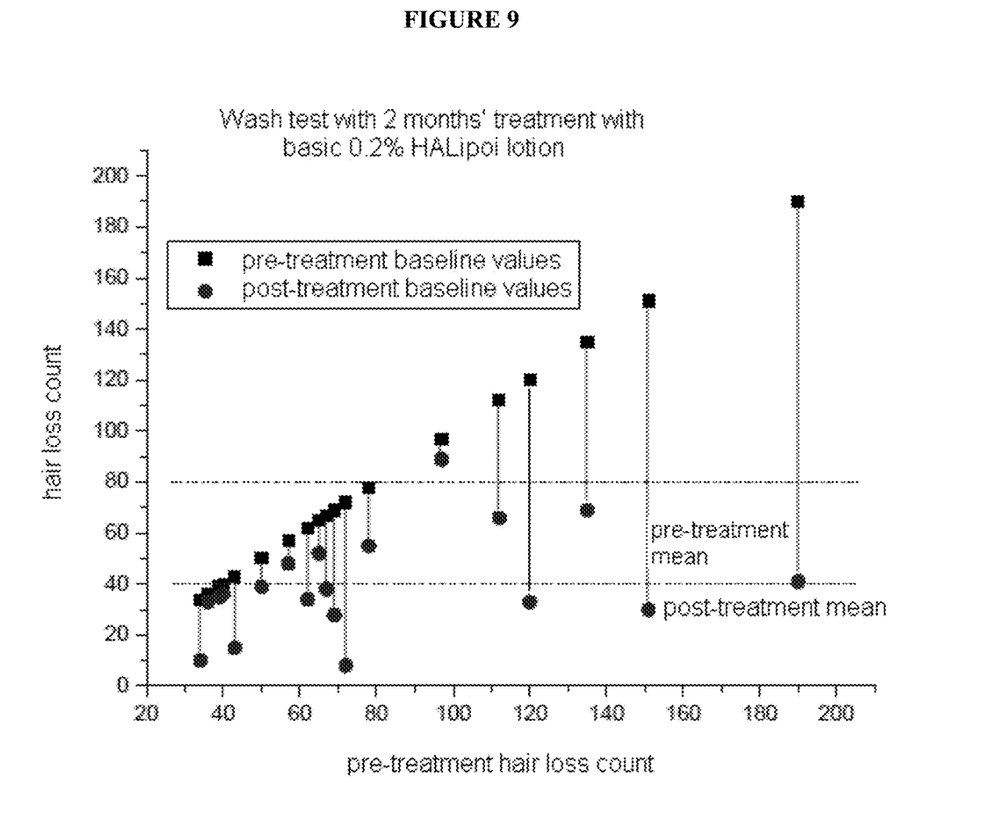
FIG. 9 shows the hair loss count before and after treatment for each subject.

The volunteers presented baseline values distributed over a wide range (34 to 190 hairs lost during washing), and consequently represent a heterogeneous case study. FIG. 9 shows the hair loss count before and after treatment for each subject. All treated subjects observed a reduction in hair loss, and the efficacy of the product was most marked in the cases where the starting situation was most severe.

The invention claimed is:

1. Topical compositions for hair care comprising
   hyaluronic acid esters, and
   a zinc salt and/or a silver salt,
   wherein the alcohol groups of the hyaluronic acid are partially esterified with lipoic acid or with lipoic acid and formic acid and wherein said zinc salt and/or said silver salt are in a molar ratio of between 0.1 and 10 of metal to the lipoic acid content.

2. Topical compositions according to claim 1, wherein the carboxyl function of the hyaluronic acid esters is present in acid form or salified with alkali metals, and the sulphate function, when present, is salified with alkali metals.

3. Topical compositions according to claim 1, wherein the molecular weight of the esters ranges from $10^3$ to $10^7$ Dalton.

4. Topical compositions according to claim 1, wherein the molecular weight of the esters ranges from $10^4$ to $10^6$ dalton.

5. Topical compositions according to claim 1 wherein the degree of esterification of lipoic acid on the hyaluronic acid hydroxyls ranges from 0.01 to 1*N, wherein N is the number of free alcohol group present in the repeating unit, while the degree of esterification of formic acid on the hyaluronic acid hydroxyls ranges from 0 to 0.20.

6. Topical compositions according to claim 1, wherein the degree of esterification of lipoic acid on the hyaluronic acid hydroxyls ranges from 0.01 to 0.2*N, wherein N is the number of free alcohol groups present in the repeating unit, while the degree of esterification of formic acid on the hyaluronic acid hydroxyls ranges from 0 to 0.20.

* * * * *